US008765737B1

(12) United States Patent
Mash et al.

(10) Patent No.: US 8,765,737 B1
(45) Date of Patent: Jul. 1, 2014

(54) METHODS AND COMPOSITIONS FOR PREPARING AND PURIFYING NORIBOGAINE

(75) Inventors: Deborah C. Mash, Miami, FL (US); Richard D. Gless, Jr., Oakland, CA (US)

(73) Assignee: DemeRx, Inc., Miami, FL (US)

( * ) Notice: Subject to any disclaimer, the term of this patent is extended or adjusted under 35 U.S.C. 154(b) by 180 days.

(21) Appl. No.: 13/104,406

(22) Filed: May 10, 2011

Related U.S. Application Data

(60) Provisional application No. 61/333,476, filed on May 11, 2010, provisional application No. 61/419,772, filed on Dec. 3, 2010.

(51) Int. Cl.
*A61K 31/55* (2006.01)

(52) U.S. Cl.
USPC ...................................... 514/214.02; 540/579

(58) Field of Classification Search
USPC ...................................... 514/214.02; 540/579
See application file for complete search history.

(56) References Cited

U.S. PATENT DOCUMENTS

| | | | |
|---|---|---|---|
| 2,813,873 A | 11/1957 | Janot et al. | |
| 3,516,989 A | 6/1970 | Sallay | |
| 3,557,126 A | 1/1971 | Sallay | |
| 3,574,220 A | 4/1971 | Sallay | |
| 3,639,408 A | 2/1972 | Nagata et al. | |
| 3,715,361 A | 2/1973 | Epstein et al. | |
| 3,875,011 A | 4/1975 | Rubenstein et al. | |
| 4,107,288 A | 8/1978 | Oppenheim et al. | |
| 4,272,541 A | 6/1981 | Kotick et al. | |
| 4,375,414 A | 3/1983 | Strahilevitz | |
| 4,444,758 A | 4/1984 | Scherschlicht et al. | |
| 4,462,941 A | 7/1984 | Lee et al. | |
| 4,464,378 A | 8/1984 | Hussain | |
| 4,499,096 A | 2/1985 | Lotsof | |
| 4,573,995 A | 3/1986 | Chen et al. | |
| 4,587,243 A | 5/1986 | Lotsof | |
| 4,604,365 A | 8/1986 | O'Neill et al. | |
| 4,620,977 A | 11/1986 | Strahilevitz | |
| 4,626,539 A | 12/1986 | Aungst et al. | |
| 4,661,492 A | 4/1987 | Lewis et al. | |
| 4,668,232 A | 5/1987 | Cordes et al. | |
| 4,737,586 A | 4/1988 | Potier et al. | |
| 4,806,341 A | 2/1989 | Chien et al. | |
| 4,857,523 A | 8/1989 | Lotsof | |
| 5,026,697 A | 6/1991 | Lotsof | |
| 5,075,341 A | 12/1991 | Mendelson et al. | |
| 5,145,684 A | 9/1992 | Liversidge et al. | |
| 5,149,538 A | 9/1992 | Granger et al. | |
| 5,152,994 A | 10/1992 | Lotsof | |
| 5,283,247 A | 2/1994 | Dwivedi et al. | |
| 5,290,784 A | 3/1994 | Qu et al. | |
| 5,316,759 A | 5/1994 | Rose et al. | |
| 5,382,657 A | 1/1995 | Karasiewicz et al. | |
| 5,426,112 A | 6/1995 | Zagon et al. | |
| 5,552,406 A | 9/1996 | Mendelson et al. | |
| 5,574,052 A | 11/1996 | Rose et al. | |
| 5,578,645 A | 11/1996 | Askanazi et al. | |
| 5,580,876 A | 12/1996 | Crain et al. | |
| 5,591,738 A | 1/1997 | Lotsof | |
| 5,618,555 A | 4/1997 | Tokuda et al. | |
| 5,703,101 A | 12/1997 | Rose et al. | |
| 5,726,190 A | 3/1998 | Rose et al. | |
| 5,760,044 A | 6/1998 | Archer | |
| 5,861,422 A | 1/1999 | Rose et al. | |
| 5,865,444 A | 2/1999 | Kempf et al. | |
| 5,925,634 A | 7/1999 | Olney | |
| 5,935,975 A | 8/1999 | Rose et al. | |
| 6,211,360 B1 | 4/2001 | Glick et al. | |
| 6,291,675 B1 | 9/2001 | Coop et al. | |
| 6,348,456 B1 * | 2/2002 | Mash et al. | 514/214.03 |
| 6,451,806 B2 | 9/2002 | Farrar | |
| 6,806,291 B1 | 10/2004 | Sunkel et al. | |
| 6,864,271 B2 | 3/2005 | Bazan et al. | |
| 7,220,737 B1 * | 5/2007 | Mash | 514/214.03 |
| 7,737,169 B2 * | 6/2010 | Corrie et al. | 514/415 |
| 7,745,479 B2 * | 6/2010 | Nettekoven et al. | 514/419 |
| 7,754,710 B2 | 7/2010 | Mash | |
| 8,178,524 B2 | 5/2012 | Mash | |
| 8,362,007 B1 * | 1/2013 | Mash et al. | 514/214.02 |
| 2003/0153552 A1 | 8/2003 | Mash et al. | |
| 2003/0158202 A1 | 8/2003 | Caldirola et al. | |
| 2006/0051317 A1 | 3/2006 | Batrakova et al. | |
| 2010/0311722 A1 | 12/2010 | Mash | |
| 2010/0311723 A1 | 12/2010 | Mash | |
| 2010/0311725 A1 | 12/2010 | Mash | |
| 2012/0083485 A1 | 4/2012 | Mash | |
| 2013/0072472 A1 * | 3/2013 | Gless et al. | 514/214.02 |

FOREIGN PATENT DOCUMENTS

| | | |
|---|---|---|
| CA | 2039197 | 9/1995 |
| DE | 22 17 132 | 10/1972 |
| GB | 0 841 697 | 7/1960 |
| GB | 0 924 042 | 4/1963 |

(Continued)

OTHER PUBLICATIONS

U.S. Appl. No. 13/165,626, filed Jun. 21, 2011, Mash.
James, "Linkers for solid phase organic synthesis", Tetrahedron 55, 1999, 4855-4946.
U.S. Appl. No. 13/104,406, filed May 10, 2011, Mash et al.
U.S. Appl. No. 13/165,626, filed Jun. 21, 2011, Mash, Deborah C.
U.S. Appl. No. 13/165,639, filed Jun. 21, 2011, Mash et al.
U.S. Appl. No. 13/165,642, filed Jun. 21, 2011, Mash et al.
U.S Appl. No. 13/198,593, filed Nov. 7, 2011, Mash et al.
U.S. Appl. No. 13/383,405, Moriarty, Robert.
U.S. Appl. No. 13/496,185, Mash, Deborah C.
Ala-Hurula et al. "Erogotamine Abuse: Results of Ergotamine Discontinuation, with Special Reference to the Plasma Concentrations", Cephalalgia, 2/4: abstract only, 1982.
Ala-Hurula et al. "Tolfenamic Acid and Ergotamine Abuse", Headache: The Journal of Head and Face Pain, 21(6): abstract only, 1981.
Alexander. "A Procedure for Drug Screening Without the Need to Transport Urines Use of Ion Exchange Papers and Hem Agglutination Inhibition", Clin Toxicol, 9(3): abstract only, 1976.
Alim et al. "Open-Label, Dose Run-Up Study of Diethylpropion in Initial Cocaine Abstinence", Clinical Neuropharmacology, 17(2): abstract only, 1994.

(Continued)

*Primary Examiner* — Peter D. Mulcahy
*Assistant Examiner* — Henry Hu
(74) *Attorney, Agent, or Firm* — Foley & Lardner LLP

(57) ABSTRACT

Disclosed are methods and compositions for purifying the non-addictive alkaloid noribogaine.

1 Claim, No Drawings

(56) References Cited

FOREIGN PATENT DOCUMENTS

| GB | 1 256 914 | 12/1971 |
|---|---|---|
| GB | 1 378 348 | 12/1974 |
| GB | 2 271 059 | 4/1994 |
| JP | 04-221315 | 8/1992 |
| WO | WO-91/18609 A1 | 12/1991 |
| WO | WO-93/20825 A1 | 10/1993 |
| WO | WO-93/25217 A1 | 12/1993 |
| WO | WO-94/06426 A1 | 3/1994 |
| WO | WO-94/14490 A1 | 7/1994 |
| WO | WO-96/03127 A1 | 2/1996 |

OTHER PUBLICATIONS

Almeida. "Use and Abuse of Alcohol and Drugs a Clinical Study of Certain Aspects of Their Interrelationship", Bol of Sanit Panam, 88(1), abstract only, 1980.
Al-Shabanah et al. "Gastric Antiulcer and Cytoprotective Effects of Cathinone, a Psychoactive Alkaloid of Khat (Catha Edulis Forsk.) and Amphetamine in Rats", Regulatory Peptides, abstract only, 1994.
Azevedo et al. "Adrenergic Nerve Degeneration Induced by Condensation Products of Adrenaline and Acetaldehyde", Naunyn-Schmiedeberg's Arch Pharmacol, 300(2): abstract only, 1977.
Bagal et al. "Modulation of Morphine-Induced Antinociception by Ibogaine and Noribogaine", Brain Research, 741(1-2): pp. 258-262, 1996.
Ban. "Adverse Effects to Psychotomimetics. Proposition of a Psychopharmacological Classification", In: Radouco-Thomas S, ed. Pharmacologie, Toxicologie, et abus des psychotomimetiques (hallucinogens)., QV 109: abstract only, 1974.
Bartlett et al. "The Alkaloids of Tabernanthe iboga. Part IV . . . sup.1 The Structures of Ibogamine, Ibogaine, Tabernanthine and Voacangine", J. Am. Chem. Soc., 80: pp. 126-136, 1958.
Batrakova. "Pluronic P85 Enhances the Delivery of Digoxin to the Brain: In Vitro and In Vivo Studies", The J. of Pharm. and Exp. Thera, 296, p. 551-557, 2001.
Baumann et al. "Comparative Neurobiology of Ibogaine and its Metabolite, 12-Hydroxyibogaimine (Noribogaine), in Rodents." Conference at New York University, Abstract only. Date Unknown.
Beaubrun. "The Diagnosis and Management of Acute Psychotic Reaction Due to Alcohol and Drugs", Caribb Med J, 36(1): abstract only, 1975.
Beck et al. "Energy-Dependent Reduced Drug Binding as a Mechanism of Vinca Alkaloid Resistance in Human Leukemic Lymphoblasts", Mol Pharmacol, 24(3): abstract only, 1983.
Benet et al. "Pharmacokinetics: Biotransformation of Drugs." In Gilman et al. Goodman and Gilman's the Pharmacological Basis of Therapeutics (1990) :13-16.
Benoist et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", Cancer Immunol Immunother, 30(5): abstract only, 1989.
Bert et al. "Non-Amphetaminic Central Stimulation by Alkaloids from the Ibogaine and Vobasine Series", Planta Med., 54(3): abstract only, 1988.
Bhargava et al. "Effects of ibogaine and noribogaine on the antinociceptive action of mu-, delta- and kappa-opioid receptor agonists in mice", Brain Research 752:234-238, 1997.
Blum et al. "Peyote a Potential Ethnopharmacologic Agent for Alcoholism and Other Drug Dependencies Possible Biochemical Rationale", Clin Toxicol, 11(4): abstract only, 1977.
Blum et al. "Possible Role of Tetrahydroisoquinoline Alkaloids in Postalcohol Intoxication States", Ann N Y Acad Sci, 273: abstract only, 1976.
Blum et al. "Putative Role of Isoquinoline Alkaloids in Alcoholism: A Link to Opiates", Alcohol Clin Exp Res, 2(2): abstract only, 1978.
Brady et al. "Analgesic Effects of Intraventricular Morphine and Enkephalins in Nondependent and Morphine-Dependent Rats", J. Pharmacol. Exp. Ther., 222(1): abstract only, 1982.
Buchi et al. "The total synthesis of iboga alkaloids", J. Am. Chem. Soc. vol. 88, p. 3099-3109, 1966.
Bundgaard. "Design of Prodrugs: Bioreversible Derivatives for Various Functional Groups and Chemical Entities." Design of Prodrugs, 1-10, 1985.
Bussel et al. "Isolated Thrombocytopenia in Patients Infected with HIV Treatment with Intravenous Gamma Globulin", Am J Hematol, 28(2): abstract only, 1988.
Caldwell et al. "The Biochemical Pharmacology of Abused Drugs. III. Cannabis, Opiates, and Synthetic Narcotics", Clin. Pharmacol. Ther., 16/6: abstract only, 1974.
Cankat. "Pharmacological Aspects of Drug Induced Headache", Funct. Neurol., 7/6: abstract only, 1992.
Cappendijk et al. "Inhibitory Effects of Ibogaine on Cocaine Self-Administration in Rats", Eur. J. Pharmacol., 241 (2-3): abstract only, 1993.
Cappendijk et al. "The Inhibitory Effect of Norharman on Morphine Withdrawal Syndrome in Rats: Comparisons with Ibogaine", Behavioural Brain Research, pp. 1-3, 1994.
Castle. "Drugs and Fibrotic Reactions—Part I", Adverse Drug React. Bull., 113: abstract only, 1985.
Chemical abstract, RN 16671-16-2 Registry, 1967.
Chemical abstract, RN 3464-63-9 Registry, 1965.
Chemical abstract, RN 481-87-8 Registry, 1952.
Chemical abstract, RN 4865-78-5 Registry, 1965.
Chemical abstract, RN 53508-36-4 Registry, 1974.
Chemical abstract, RN 57511-56-5 Registry, 1975.
Chemical abstract, RN 77123-15-0 Registry, 1980.
Chemical abstract, RN 83-74-9 Registry, 1934.
Chemical abstract, RN 88660-07-5 Registry, 1983.
Chemical abstract, RN 88660-09-7 Registry, 1983.
Cherny et al. "Opioid responsiveness of cancer pain syndromes caused by neuropathic or nociceptive mechanisms: a combined analysis of controlled, single-dose studies", Neurobiology 44:857-861, 1994.
Cheze et al. "Determination of ibogaine and noribogaine in biological fluids and hair by LC-MS/MS after *Tabernanthe iboga* abuse", Forensic Science International, Elsevier Scientific Publishers Ireland Ltd, IE, vol. 176. No. 1, pp. 58-66, 2007.
Criel et al. "Drug Dependent Red Cell Antibodies and Intravascular Haemolysis Occurring in Patients Treated with 9 Hydroxy-Methyl-Ellipticinium", Br J Haematol, 46(4): abstract only, 1980.
Damstrup et al. "Retroperitoneal Fibrosis After Long-Term Daily Use of Ergotamine", Int. Urol. Nephrol., 18/3: abstract only, 1986.
Deecher et al. "Mechanisms of Action of Ibogaine and Harmaline Congeners Based on Radioligand Binding Studies", Brain Research, 571(2): pp. 242-247, 1992.
Diener et al. "Analgesic-Induced Chronic Headache Long-Term Results of Withdrawal Therapy", J Neurol, 236(1): abstract only, 1989.
Dierckx et al. "Intraarterial Sodium Nitroprusside Infusion in the Treatment of Severe Ergotism", Clin. Neuropharmacol., 9/6: abstract only, 1986.
Dzoljic et al. "Effect of Ibogaine on Naloxone-Precipitated Withdrawal Syndrome in Chronic Morphine-Dependent Rats", Arch. Int. Pharmacodyn., 294:64-70, 1988.
Eberwine et al. "Molecular Analysis of Cellular Responses to Opiate Use", Fidia Res. Found. Symp. Ser., 7(Neurotransm. Regul. Gene Transcr.): abstract only, 1991.
Elkind. "Drug Abuse and Headache", Med Clin North Am, 75(3): abstract only, 1991.
Evenson. "Developments in Therapeutic Drug Monitoring and Alkaloid Analysis", Fed Proc, 34(12): abstract only, 1975.
Faglia et al. "Dihydroergocryptine in Management of Microprolactinomas", J Clin Endocrinol Metab, 65(4): abstract only, 1987.
Fairchild et al. "Keynote Address: Multidrug Resistance: A Pleiotropic Response to Cytotoxic Drugs", Int. J. Radiat. Oncol. Biol. Phys., 20/2: abstract only, 1991.
Finkle. "Phencyclidine Identification by Thin-Layer Chromatography. A Rapid Screening Procedure for Emergency Toxicology", Am. J. Clin. Pathol., 70/2: abstract only, 1978.

(56) References Cited

OTHER PUBLICATIONS

Fonne-Pfister et al. "Xenobiotic and Endobiotic Inhibitors of Cytochrome P-450db1 Function, the Target of the Debrisoquine / Sparteine Type Polymorphism", Biochem. Pharmacol., 37(20): abstract only, 1988.

Frances et al. "Effects of Ibogaine on Naloxone-Precipitated Withdrawal in Morphine-Dependent Mice", Fundam Clin Pharmacol, 6(8-9): abstract only, 1992.

Gabr et al. "Changes in Absolute Amount of Alkaloids in Datura-Metel Treated with Certain Growth Regulators", Herba Pol, 21(2): abstract only, 1975.

Garcia et al. "Chronic pain states: pathophysiology and medical therapy", Seminars in Arthritis and Rheumatism, 27:1-16, 1997.

Gennaro. "Remington: The Science and Practice of Pharmacy", Mack Publishing Col., vol. II, pp. 1736 & 1814, 1995.

George et al. "Palliative medicine", Postgrad, Med. Journal, vol. 69, pp. 426-449, 1993.

Gifford et al. "Effect of Chronic Cocaine Treatment on D SUB 2 Receptors Regulating the Release of Dopamine and Acetylcholine in the Nucleus Accumbens and Striatum", Pharmacology, Biochemistry and Behavior, 41(4): abstract only, 1992.

Glick et al. "Effects of iboga Alkaloids on Morphine and Cocaine Self-Administration in Rats: Relationship to Tremorigenic Effects and to Effects on Dopamine Release in Nucleus Accumbens and Striatum." Brain Research, 657:14-22, 1994.

Glick et al. "Effect of Ibogaine on Acute Signs of Morphine Withdrawal in Rats: Independence from Tremor", Neuropharmacology, 31/5: abstract only, 1992.

Glick et al. "Effects of Aftereffects of Ibogaine on Morphine Self-Administration in Rats", European Journal of Pharmacology, 195(3): abstract only, 1991.

Glick et al. "Ibogaine-like effects of noribogaine in rats", Brain Research, 713:294-297, 1996.

Glick et al. "Local Effects of Ibogaine on Extracellular Levels of Dopamine and Its Metabolites in Nucleus Accumbens and Striatum: Interactions with D-Amphetamine", Brain Research, 628(1-2): abstract, 1993.

Gold et al. "Effect of Methadone Dosage on Clonidine Detoxification Efficacy", Am. J. Psychiatry, 137/3: abstract only, 1980.

Gothoni. "Harmine-, Lon-954- and 5-Hydroxytryptophan-Induced Tremors in Rats Withdrawn from Ethanol", Acta Pharmacol Toxicol, 57(1): abstract only, 1985.

Gross. "Effect of Ergot Alkaloids on Serum Prolactin in Non-Psychotic Organic Brain Syndrome of the Elderly", Exp Aging Res, 5(4): abstract only, 1979.

Gunn. "Relations Between Chemical Constitution, Pharmacological Actions, and Therapeutic Uses, in the Harmine Group of Alkaloids", From the Pharmacological Laboratory, University of Oxford:379-396, 1935.

Haber et al. "Tetrahydroisoquinolines—Endogenous Products After Chronic Alcohol Abuse", Pharmazie, 47/1: abstract only, 1992.

Halikas et al. "Treatment of Crack Cocaine Use with Carbamazepine", Am J Drug Alcohol Abuse, 18(1): abstract only, 1992.

Hanks. "Opioid-responsive and opioid-non-responsive pain in cancer", British Medical Bulletin 47:718-731, 1991.

Hardman et al. "Goodman & Gilman's The Parmacological Basis of Therapeutics" (9th ed, 1996) p. 51 and 57-58.

Harsing, Jr. et al. "Evidence that Ibogaine Releases Dopamine from the Cytoplasmic Pool in Isloated Mouse Striatum", Journal of Neural Transmission General Section, 96(3): abstract only, 1994.

Hearn et al. "Identification and Quantitation of Ibogaine and an o-Demethylated Metabolite in Brain and Biological Fluids Using Gas Chromatography-Mass Spectrometry." J. Analytical Toxicology, 19:427-434, 1995.

Heel et al. "Buprenorphine: A Review of Its Pharmacological Properties and Therapeutic Efficacy", Drugs, 17(2): abstract only, 1979.

Henry et al. "Reversible Cerebral Arteriopathy Associated with the Administration of Ergot Derivatives", Cephalalgia, 4/3: abstract only, 1984.

Ho et al. "Metabolism of Harmaline in Rats." Biochemical Pharmacology, 20:1313-1319, 1971.

Hoes. "Clinical Criteria for the Selection of Anxiolytics", Tijdschr. Ther. Geneesm. Onderz., 9/9: abstract only, 1984.

Holbrook. "Nicotine Addiction." In Isselbacher et al. Harrison's Principles of Internal Medicine:2433-2437, 1994.

Holzner et al. "The Neuroleptic Sleeping Course in Chronic Headache", Therapiewoche, 35/36: abstract only, 1985.

Huang et al. "Cytotoxicity and Sister Chromatid Exchanges Induced in Vitro by Six Anticancer Drugs Developed in the People's Republic of China", J Natl Cancer Inst, 71(4): abstract only, 1983.

Hubens et al. "Chronic Intake of a Hydrogenated Ergot Alkaloid Causing Peripheral Vascular Ischemia—A Case Report", Vasc. Surg., 21/4: abstract only, 1987.

Huffman et al. "A Formal Synthesis of (±)-Ibogamine", J. Org. Chem. vol. 50, pp. 1460-1464, 1985.

Isler. "Treatment of Headache", Schweiz. Med. Wochenschr., 114/35: abstract only, 1984.

Jaffe. "Drug Addiction and Drug Abuse." In Gilman et al. Goodman and Gilman's The Pharmacological Basis of Therpeutics:522-523, 559-568, 1990.

Jaffe. "Psychopharmacology and Opiate Dependence", U.S. Public Health Serv. Publ., 1957-1967:1836, 1967.

Jane et al. "High-Performance Liquid Chromatographic Analysis of Basic Drugs on Silica Columns Using Non-Aqueous Ionic Eluents. II. Application of UV, Fluorescence and Electrochemical Oxidation detection", J. Chromatogr., 323(2): abstract only, 1985.

Jansen et al. "Ethnopharmacology of Kratom and the Mitragyna Alkaloids", J Ethnopharmacol, 23(1): abstract only, 1988.

Janzen. "History of Use of Psychotropic Drugs in Central Africa", Psychotropes, 1/2: abstract only, 1983.

Justins. "Management strategies for chronic pain", Annals of the Rheumatic Diseases, vol. 55, pp. 588-596, 1996.

Kalix. "Khat: A Plant with Amphetamine Effects", J Subst Abuse Treat, 5(3): abstract only, 1988.

Kalix. "Pharmacological Properties of the Stimulant Khat", Pharmacol. Ther., 48/3: abstract only, 1990.

Keefner. "A Gas Chromatography-Mass Spectrometry (GCMS) Method for Ibogaine", Society for Neuroscience Abstracts, 19(1-3): abstract only, 1993.

Keller et al. "Modulation of Neopterin Release by Human Kupffer Cells in Culture: Possible Implication in Clinical Monitoring of HIV-Seropositive Subjects", Cells Hepatic Sinusoid, 3: abstract only, 1991.

Knoll. "Azidomorphines and Homopyrimidazols: A New Approach to the Ideal Analgetic", Acta Physicol Pharmacol Bulg, 3(2): abstract only, 1977.

Knoll. "Azidomorphines: A New Family of Potent Analgesics with Low Dependence Capacity", Prog. Neuro-Psychopharmacol., 3/1-3: abstract only, 1979.

Koch et al. "Drug-Induced Liver Injury in Liver Biopsies of the Years 1981 and 1983, their Prevalence and Type of Presentation", Path. Res. Pract., 179: abstract only, 1985.

Konig. "Psychiatric Intensive Therapy After Acute Alkaloid Withdrawal Syndrome", Infusionsther Klin Ernahr, 6(1): abstract only, 1979.

Kornetsky, "Pharmacology Drugs Affecting Behavior", New York, John Wiley & Sons, pp. 186-187, 1976.

Kostowski et al. "The Effects of Some Hallucinogens on Aggressiveness of Mice and Rats" Pharmacology vol. 7, pp. 259-263, 1972.

Krug. "Cocaine Abuse: Historical, Epidemiologic, and Clinical Perspectives for Pediatricians", Advances in Pediatrics, 36:369-406, 1989.

Kupers et al., "Morphine differentially affects the sensory and affective pain ratings in neuorgenic and idiopathic forms of pain." Pain 47:5-12, 1991.

Lakoski et al. "Electrophysiologic Characterization of an Ibogaine Metabolite in Dorsal Raphe Nucleus and Hippocampus." Soc. Neurosc. 21:716 Abstract only, 1995.

Larson-Prior et al. "Electrophysiologic Characterization of an Ibogaine Metabolite in the Cerebellar Cortex." Soc. Neurosc. 21:716 Abstract only, 1995.

(56) References Cited

OTHER PUBLICATIONS

Lemontt et al. "Increase MDR Gene Expression and Decreased Drug Accumulation in Multidrug-Resistant Human Melanoma Cells", Cancer Res, 48(22): abstract only, 1988.
Leoni et al. "Effect of Cocaine and Morphine on Neutral Endopeptidase Activity of Human Peripheral Blood Mononuclear Cells Cultures with Lectins", Cell Biochem Funct, 11(3): abstract only, 1993.
Lerida et al. "Incidence of Morphine Withdrawal and Quasi-Abstinence Syndrome in a Model of Chronic Pain in the Rat", Neurosci., 81(1-2): abstract only, 1987.
Lewis et al. "Adverse Reactions and Interactions with .beta.-Adrenoceptor Blocking Drugs", Med. Toxicol., 1/5: abstract only, 1986.
Lewis et al. "Narcotic Analgesics and Antagonists", Annu Rev Pharmacol, 11: abstract only, 1971.
Licht et al. "Induction of Multiple-Drug Resistance During Anti-Neoplastic Chemotherapy In-Vitro", Int J Cancer, 49(4): abstract only, 1991.
Ling et al., "Drugs of Abuse-Opiates", in Addtiction Medicine [Special Issue], Western Journal of Medicine, 152:565-572, 1990.
Low et al. "Effects of Acronycine and Cytouchalasin B on the Division of Rat Leukemia Cells", Exp Cell Res, 131(1): abstract only, 1981.
Ma et al. "Inhibition of Respiratory Burst Activity in Alveolar Macrophages by Bisbenzylisoquinoline Alkaloids: Characterization of Drug-Cell Interaction", Exp. Lung Res., 18/6: abstract only, 1992.
Maisonneuve et al. "Interactions of Ibogaine and D-Amphetamine: in vivio Microdialysis and Motor Behavior in Rats." Brain Research 579:87-92, 1992.
Maisonneuve et al. "Acute and Prolonged Effects of Ibogaine on Brain Dopamine Metabolism and Morphine-Induced Locomotor Activity in Rats", Brain Research, 575(1): abstract only, 1992.
Maisonneuve et al. "Interactions Between Ibogaine, a Potential Anti-Addictive Agent, and Morphine: an in Vivo Microdialysis Study", Eur. J. Pharmacol., 199(1): abstract only, 1991.
Martellotta et al. "Effects of the Calcium Antagonist Isradipine on Cocaine Intravenous Self-Administration in Rats", Psychopharmacologia, 113(3-4): Abstract only, 1994.
Martin et al. "Neuropathic Pain in Cancer Patients: Mechanisms, Syndromes, and Clinical Controversies," Journal of Pain and Symptom Management 14(2):99-117, 1997.
Mash et al, "Properties of Ibogaine and its Principle Metabolite (12-hydroxyibogamine) at the MK-801 binding site of the NMDA receptor complex," Neuroscience Letters, 192, 53-56, 1995.
Mash et al. "Ligand Binding Profiles of Ibogaine and its O-demethylated Metabolite Noribogaine: Implications for Developing Novel Multi-target Anti-addiction Agents." Soc. Neurosc. (1995) 21:717 Abstract only.
Mash et al. "Preclinical screening of an ibogaie metabolite (noribogaine) on cocaine-induced hyperlocomotion and cocaine self-administration." Soc. Neurosc. 22:1929 Abstract only, 1996.
Mash et al. "Ibogaine in the Treatment of Heroin Withdrawal," The Alkaloids 56:1-17, 2001.
Mateer et al. "Reversible Ipecac Myopathy", Arch. Neurol., 42/2: abstract only, 1985.
Matharu et al. "Preformulation and Development of Ibogaine Injection for the Treatment of Drug Abuse", Pharmaceutical Research, 10: abstract only, 1993.
Mattingly et al. "Selective Antagonism of Dopamine D Sub1 and D Sub 2 Receptors Does Not Block the Development of Behavioral Sensitization to Cocaine", Psychopharmacologia, 114(2): abstract only, 1994.
McNeish et al. "The 5-HT Sub 3 Antagonist Zacopride Attenuates Cocaine-Induced Increases in Extracellular Dopamine in Rat Nucleus Accumbens", Pharmacology, Biochemistry, and Behavior, 45(4): abstract only, 1993.
Melchior et al. "Preference for Alcohol Evoked by Tetra Hydro Papaveroline Chronically Infused in the Cerebral Ventricle of the Rat", Pharmacol Biochem Behav, 7(1): abstract only, 1977.

Mendelson et al. "Cocaine and Other Commonly Abused Drugs." In Isselbacher et al. Harrison's Principles of Internal Medicine:2429-2433, 1994.
Menzies et al. "Gangrene of the Small Bowel: A Complication of Methysergide Therapy", Aust. N. Z. J. Surg., 52/5: abstract only, 1982.
Metelitsa. "Pharmacological Agents in Controlling Smoking", Biull Vsesoiuznogo Kardiol Nauchn Tsentra, 10(1): abstract only, 1987.
Millan, "k-Opioid Receptors and Analgesia," Trendes in Pharmacogicla Sciences, 11, pp. 70-76, 1990.
Mizuhashi et al. "Antitumor Activities of IKP-104 A 4-1H Pyridizinone Derivative on Cultured and Implanted Tumors", Jpn J Cancer Res, 81(12): abstract only, 1990.
Montefiori et al. "In Vitro Evaluation of Mismatched Double-Stranded RNA (Ampligen) for Combination Therapy in the Treatment of Acquired Immunodeficiency Syndrome", AIDS Res Hum Retroviruses, 5(2): abstract only, 1989.
Mulamba et al., Alcaloides de Tabernanthe Pubescens. Journal of Natural Products, vol. 44, No. 2, p. 184-189, 1981.
Naranjo. "Ibogaine in psychotherapy: psychoanalysis according to Naranjo", part IV, pp. 1-2. http://www.nettuno.it/fiera/electric.italy/bwitif:html.
Nishiyama et al. "Expression of the Multidrug Transporter, P-Glycoproteiin, in Renal and Transitional Cell Carcinomas", Cancer, 71(11):3611-3619, 1993.
Nooter et al. "Multidrug Resistance (MDR) Genes in Haematological Malignancies", Cytotechnology, 12(1-3): abstract only, 1993.
Nunn-Thompson et al. "Pharmacotherapy for Making Cessation", Clin Pharm, 8(10): abstract only, 1989.
Obach et al., "Cythochrome P4502D6 Catalyzes the O-Demethylation of the Psychoactive Alkaloid Ibogaine to 12-Hydroxyibogamine" Drug Metabolism and Disposition 26(8):764-768, 1998.
O'Hearn et al. "Degenration of Prukinje Cells in Parasagittal Zones of the Cerebellar Vermis After Treatment with Ibogaine of Harmaline", Neuroscience, 55(2): abstract only, 1993.
O'Hearn et al. "Ibogaine Induces Glial Activation in Parasagittal Zones of the Cerebellum", Neuroreport, 4/3: abstract only, 1993.
Pablo et al, "Noribogaine Stimulates Naloxone-Sensitive[35S]GTPgammaS Binding," NeuroReport, 9, pp. 109-114. (Website Publication Date of Dec. 20, 1997.), 1998.
Pacifici et al. "Immunological Effect of Cocaine and Host Resistance in Mice", Int J Immunother, 8(2): abstract only, 1992.
Palyi. "Survivial Responses to New Cytostatic Hexitols of P388 Mouse and K562 Leukemia Cells in Vitro", Cancer Treat. Rep., 70(2): abstract only, 1986.
Pantazis et al. "Efficacy of Camptothecin Congeners in the Treatment of Human Breast Carcinoma Xenografts", Oncology Research, 5(8): abstract only, 1994.
Pehek. "Effects of Cathinone and Amphetamine on the Neurochemistry of Dopamine in Vivo", Neuropharmacology, 29/12: abstract only, 1990.
Perera et al. "Tertiary Indole Alkaloids of Tabernaemontana Dichotoma Seeds", Planta Med., 49/1: abstract only, 1983.
Perrin. "Clinical Pharmacokinetics of Ergotamine in Migraine and Cluster Headache", Clin. Pharmacokin., 10/4: abstract only, 1985.
Popik et al. "NMDA Antagonist Properties of the pUtative Antiaddictive Drug, Ibogaine", Journal of Pharmaceutical and Experimental Therapeutics, 275(2), 753-760, 1995.
Popik et al. "The Putative Anti-Addictive Drug Ibogaine is a Competitive Inhibitor of ( SUP 3 H) Binding to the NMDA Receptor Complex", Psychopharmacologia, 114(4): abstract only, 1994.
Popik et al. "100 Years of Ibogaine: Neurochemical and Pharmacological Actions of a Putative anti-addictive Drug", Pharmacological Reviews 47(2), pp. 235-253, 1995.
Pulvirenti et al. "Lisuride Reduces Intravenous Cocaine Self-Administration in Rats", Pharmacology, Biochemistry and Behavior, 47(4): abstract only, 1994.
Qiu et al. "The Influence of Chronic Nicotine Treatment on Stress-Induces Gastric Ulceration and Emptying Rate in Rats", Experientia, 48(4): abstract only, 1992.

(56) References Cited

OTHER PUBLICATIONS

Rezvani et al. "Noribogaine, a Primary Ibogaine Metabolite, Reduces Alcohol Intake in P and Fawn-Hooded Rats." RSA Annual Scientific Meeting Abstract only, 1995.
Rezvani et al. "Reduction of Alcohol Intake in Alcohol Preferring Fawn-hooded and P Rats by Noribogaine, the Primary Metabolite of Ibogaine." NIDA Monograph Series (1996) 162:281 Abstract only.
Ricceri et al. "Postnatal cocaine Esposure Affects Neonatal Passive Avoidance Performance and Cholinergic Development in Rats", Pharmacology, Biochemistry and Behavior, 45(2): abstract only, 1993.
Rodriguez et al. "Cocaine Adminstration Prior to Reactivation Facilitates Later Acquisition of an Avoidance Response in Rats", Psychopharmacologia, 112(2-3): abstract only, 1993.
Rosenmund et al. "Ibogamin, Ibogain and Epiibogamin" Chem. Ber. vol. 108, p. 1871-1895, 1975. structures and abstract only.
Sachs et al. "Corneal Complications Associated with the Use of Crack Cocaine", Ophthalmology, 100(2): abstract only, 1993.
Salmoiraghi et al. "Effects of LSD 25, BOL 148, Bufotenine, Mescaline and Ibogaine on the Potentiation of Hexobarbital Hypnosis Produced by Serotonin and Reserpine." J. Pharm and Exp Ther. vol. 120. No. 1, pp. 20-25, 1957.
Samadi-Baboli et al. "Preparation of Low Density Lipoprotein-9-Methoxy-Illipticin Complex and Its Cytotoxic Effect Against L1210 and p. 388 Leukemic Cells in Vitro", Eur J Cancer Clin Oncol, 25(2): abstract only, 1989.
Saper et al. "Ergotamine Tartrate Dependency: Features and Possible Mechanisms", Clin. Neuropharmacol., 9/3: abstract only, 1986.
Schecter et al. "Comparison of the Behavioral Effects of Ibogaine from Three Sources: Mediation of Discriminative Activity", European Jornal of Pharmacology, 249(1): abstract only, 1993.
Schneider et al. "Analysis of the Cardiovascular Action of Ibogaine Hydrochloride (1)" Arch. Int. Pharmacodyn. vol. 110, pp. 92-102, 1957.
Schneider et al., Neuropharmacological Studies of Ibogaine: An Indole Alkaloid with Central Stimulant Properties' Ann. of N.Y. Acad. Sci. vol. 66, pp. 765-776, 1957.
Schneider et al., "Potentiation Action of Ibogaine on Morphine Analgesia" Experiential vol. 12, pp. 323-324, 1956.
Schnider et al. "Use and Abuse of Analgesics in Tension-Type Headache", Cephalalgia, 14/2: abstract only, 1994.
Schuckit et al. "Opioid Drug Use." In Isselbacher et al. Harrison's Principles of Internal Medicine :2425-2429, 1994.
Schuckit. "Alcohol and Alcoholism." In Isselbacher et al. Harrison's Principles of Internal Medicine :2420-2425, 1994.
Seeber et al. "In Vivo Resistance Towards Anthracyclines, Etoposide, and Cis-Diamminedichloroplatinum (II)", Cancer Res., 42(11): abstract only, 1982.
Sehested et al. "The Carboxylic Ionophore Monensin Inhibits Active Drug Efflux and Modulates In-Vitro Resistance in Daunorubicin Resistant Enrlich Ascites Tumor Cells", Biochem Pharmacol, 37(17): abstract only, 1988.
Sershen et al. "Ibogaine Antagonizes Cocaine-Induced Locomotor Stimulation in Mice", Life Sci., 50(15): abstract only, 1992.
Sershen et al. "Ibogaine Reduces Amphetamine-Induced Locomotor Stimulation in C57BL/6By Mice, but Stimulates Locomotor Activity in Rats", Life Sci., 51(13): abstract only, 1992.
Sershen et al. "Ibogaine Reduces Preference for Cocaine Consumption in C57BL/6By Mice", Pharmacol., Biochem. Behav., 47(1): abstract only, 1994.
Shen et al. "Antagonists at Excitatory Opioid Receptors on Sensory Neurons in Culture Increase Potency and Specificity of Opiate Analgesics and Attenuate Development of Tolerance / Dependence", Brain Research, 636(2): abstract only, 1994.
Sheppard. "A Preliminary Investigation of Ibogaine: Case Reports and Recommendations for Further Study", J. Subst. Abuse Treat., 11/4: abstract only, 1994.
Shir et al., "Neuropathic pain unrelieved by morphine, alleviated by haloperidol" Harefuah 118(8):452-454, Abstract only, 1990.
Shook et al. "A cyclic Somatostatin Analog that Precipitates Withdrawal in Morphine-Dependent Mice", NIDA Res. Monogr., 76(Probl. Drug Depend.): abstract only, 1987.
Sinkula et al. "Rationale for Design for Biologically Reversible Drug Derivatives: Prodrugs." Journal of Pharmaceutical Sciences, 64(2):181-210, 1975.
Slotkin et al. "A Model of Harmine Metabolism in the Rat." The Journal of Pharmacology and Experimental Therapeutics, 174(3):456-462, 1970.
Slotkin et al. "Blood Levels and Urinary Excretion of Harmine and its Metabolites in Man and Rats." The Journal of Pharmacology and Experimental Therapeutics, 173(1):26-30, 1970.
Slotkin et al. "Urinary Metabolites of Harmine in the Rat and their Inhibition of Monoamine Oxidase." Biochemical Pharmacology 19:125-131, 1970.
Sloviter et al. "A Common Mechanism of Lysergic Acid, Indolealkylamine and Phenethylamine Hallucinogens: Serotonergic Mediation of Behavioral Effects in Rats" J. Pharm. Exp. Ther. vol. 214, No. 2, pp. 231-238, 1980.
Smith. "Interaction of Biogenic Amines with Ethanol", Adv Exp Med Biol, 56: abstract only, 1975.
Solinas et al. "Solid-supported reagents and catch-and-release techniques in organic synthesis". Synthesis 20070816 De LNKDDOI:10. 1055/S-2007-983806, No. 16., pp. 2409-2453, 2007.
Stella. "Pro-drugs: An Overview and Definition." Prodrugs As Novel Drug Delivery System. ACS Symposium Series :1-115, 1975.
Stella. "Pro-drugs as Novel Drug Delivery Systems", Higuchi, T. et al., ed. (American Chemical Society, Washington), pp. 1-49, 1975.
Sugiyama et al. "Quantitative Analysis of Cell-Kill Effects of Anticancer Drugs: Consideration of Both In Vitro and In Vivo Expreimental Systems", Gan to Kagaku Ryoho, 14(12): abstract only, 1987.
Tarnower et al. "Ergotism Masquerading as Arteritis", Postgrad Med, 85(1): abstract only, 1989.
Teoh et al. "Buprenorphine Effects on Morphine- and Cocaine-Induced Subjective Responses by Drug—Dependent Men", Journal of Clinical Psychopharmacology, 14(1): abstract only, 1994.
Tfelt-Hansen et al. "Nitroglycerin for Ergotism. Experimental Studies in Vitro and in Migraine Patients and Treatment of an Overt Case", Eur. J. Clin. Pharmacol., 22/2: abstract only, 1982.
Torrenegra et al. "Alkaloids of *Stemmadenia grandiflora*", Phytochemistry, 27(6): pp. 1843-1848, 1988.
Tsuruo. "Multidrug Resistance: A Transport System of Antitumor Agents and Xenobiotics", Princess Takamatsu Symp, 21: abstract only, 1990.
Uldry et al. "Cerebrovascular Accidents in Relation to Drug Consumption or Drug Abuse", Schweiz Rundsch Med Prax, 78(23): abstract only, 1989.
Valadez et al. "Persistence of the Ability of Amphetamine Preexposure to Facilitate Acquistion of Cocaine Self-Administration", Pharmacology, Biochemistry and Behavior, 47(1): abstract only, 1994.
Valencia et al. "Obovatine, a new bisindole alkaloid from *Stemmadenia obovata*", Journal of Natural Products, 58(1):pp. 134-137, 1995.
Vescovi et al. "Successful Treatment of Opiate Withdrawal Using Lysine Acetylsalicylate", Curr. Ther. Res., Clin. Exp., 33/5: abstract only, 1983.
Villalba et al. "Uses and Abuses of Ipecacuana Syrup", Farm. Clin., 9/1: abstract only, 1992.
Wells et al. "Recognition and Treatment of Arterial Insufficiency from Cafergot", J. Vasc. Surg., 4/1: abstract only, 1986.
Whitaker et al. "High Affinity 3H-Serotonin Binding to Caudate: Inhibition by Hallucinogenic and Serotonergic Drugs", Psychopharmacology, vol. 59, pp. 1-5, 1978.
Whitaker et al., "Selective Labeling of Serotonin Receptors by d'(3H)Lysergic Acid Diethylamide in Calf Caudate", Proc. Natl. Acad. Sci., USA vol. 75, No. 12, pp. 5783-5787, 1978.
Whittaker et al. "Recurrent Laryngeal Nerve Paralysis in Patients Receiving Vincristine and Vinblastine", Br Med J, 1(6071): abstract only, 1977.
Widler et al. "Pharmacodynamics and Pharmacokinetics of Khat: a Controlled Study", Clin. Pharmacol. Ther., 55/5: abstract only, 1994.

(56) References Cited

OTHER PUBLICATIONS

Wildmann. "Heterocycles as Physiological Ligands for the Benzodiazepine Receptor and for Other Binding Sites", Pharmacol Res, 21(6): abstract only, 1989.

Williams, Jr. et al. "The 'Alice in Wonderland' Experience Ergot Alkaloid Therapy for Prolactin-Secreting Pituitary Tumors", West. J. Med., 138/3: abstract only, 1983.

Wishart et al. "Is Multidrug Resistance Relevant in Breast Cancer", Eur. J. Surg. Oncol., 17/5: abstract only, 1991.

Witt et al. "Pharmacodynamic and Pharmacokinetic Characterization of Poly(Ethylene glycol) Conjugation to Met-Enkephalin Analog [$_D$-Pen$^2$,$_D$-Pen$^5$]-enkephalin (DPDPE)", J. of Pharm. and Exp. Thera., 298(2), pp. 848-856, 2001.

Witt et al. "Pluronic P85 Block Copolymer Enhances Opioid Pepetide Analgesia", J. of Pharm. and Exp. Thera., 303(2), pp. 760-767, 2002.

Worz. "Effects and Risks of Psychotropic and Analgesic Combinations", Am. J. Med., 75/5A: abstract only, 1983.

Zetler et al. "Pharmacokinetics in the Rat of the Hallucinogenic Alkaloids Harmine and Harmaline." Naunyn-Schmiedeberg's Arch. Pharmacol., 285, 273-292, 1974.

Zetler et al. "Cerebral Pharmacokinetics of Tremor-Producing Harmala and Iboga Alkaloids" Pharmacology vol. 7, No. 4, pp. 237-248, 1972.

Greenwald, et al., "Poly(ethylene glycol) conjugated drugs and prodrugs: a comprehensive review," Crit. Rev. Ther. Drug Carrier Syst., (2000), 17(2):101-161.

International Search Report and Written Opinion dated Oct. 4, 2012 in related PCT Application Serial No. PCT/US2012/022255.

Interantional Search Report for PCT/US2011/045081 dated Oct. 4, 2011.

Yang, et al., "Prodrug based optimal drug delivery via membrane transporter/receptor," Expert. Opin. Biol. Ther., (2001), 1(2):159-175.

Cheze, et al., (2007) "Determination of ibogaine and noribogaine in biological fluids and hair by LC-MS/MS after *Tabernanthe iboga* abuse", Forensic Science International, pp. 58-66, vol. 176-1, Elsevier Scientific Publishers Ireland Ltd,. IE.

Layer, et al., (1996) "Structurally modified ibogaine analogs exhibit differing affinities for NMDA receptors", European Journal of Pharmacology, pp. 159-165, vol. 309.

Solinas et. al., (2007) "Solid supported reagents and catch-and-release techniques in organic synthesis", Synthesis, pp. 2409-2453, vol. 16.

Stella. (1975) "Pro-drugs: An Overview and Definition." Prodrugs as Novel Drug Delivery System, ACS Symposium Series, pp. 1-115.

Database Registry (Online), Chemical Abstracts Service, Columbus Ohis, US Nov. 16, 1984, "ibogamine-18-carboxylic acid, 12-methoxy-,potassium sal," XP002638006, Database accession No. 5500-12-9.

Snyder, et al., "Practical HPLC Method Development", 1997, 2nd Ed., pp. 214-218, 266, 267, 282 & 283, John Wiley & Sons, Inc.

Stahl, et al., "Handbook of Pharmaceutical Salts", 1998, p. 250 John Wiley & Sons.

First Office Action for Chinese Appl. No. 201180038173.7, dated Mar. 25, 2014 (with English translation).

Niemann et al, "The Isolation of Rupicoline and Montanine, Two Pseudoindoxyl Alkaloids of Tabernaemontana Rupicola Benth", The Journal of Organic Chemistry, 31(7):2265-2269.

\* cited by examiner

METHODS AND COMPOSITIONS FOR PREPARING AND PURIFYING NORIBOGAINE

CROSS-REFERENCE TO RELATED APPLICATIONS

This application claims priority under 35 U.S.C. §119(e) to U.S. Provisional Patent Application Ser. No. 61/333,476, filed on May 11, 2010, and to U.S. Provisional Patent Application Ser. No. 61/419,772, filed on Dec. 3, 2010, both of which applications are incorporated by reference herein in their entirety.

FIELD OF THE INVENTION

This invention relates generally to methods and compositions for purifying the non-addictive alkaloid noribogaine.

STATE OF THE ART

Noribogaine is a well known derivative of ibogaine and is sometimes referred to as 12-hydroxyibogaine. It is a metabolite of ibogaine. U.S. Pat. No. 2,813,873 claims noribogaine albeit as "12-O-demethylibogaine" while providing an incorrect structural formula for ibogaine. The structure of noribogaine has now been thoroughly evaluated and is found to combine the features of tyrptamine, tetrahydrohavaine and indolazepines. Noribogaine can be depicted by the following formula:

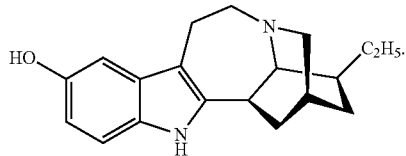

Noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737).

Conventionally, noribogaine is prepared by demethylation of naturally occurring ibogaine:

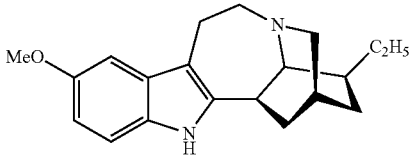

which is isolated from *Tabernanth iboga*, a shrub of West Africa. Demethylation may be accomplished by conventional techniques such as by reaction with boron tribromide/methylene chloride at room temperature followed by conventional purification.

Ibogaine possesses hallucinogenic properties. It is a Schedule 1-controlled substance as provided by the US Food and Drug Administration. Accordingly, methods for preparing noribogaine from ibogaine require high levels of assurance that contamination with unacceptable levels of ibogaine is avoided. As above, a one-step method for preparation of noribogaine from ibogaine via demethylation does not provide the requisite assurance that ibogaine will consistently be removed as a potential contaminant.

Accordingly, there is an ongoing need to provide a method for preparing noribogaine from ibogaine wherein any ibogaine contamination of noribogaine can be effectively and repeatedly minimized.

SUMMARY OF THE INVENTION

This invention provides methods and compositions for the preparation of noribogaine wherein contamination by ibogaine is predictably reduced to acceptable levels. In particular, this invention employs the use of solid supports to effect separation of noribogaine from ibogaine such that any ibogaine contamination is significantly reduced if not essentially eliminated.

Accordingly, in one of its method aspects, this invention is directed to a method for preparing and purifying noribogaine which method comprises:
 a) converting ibogaine to noribogaine wherein the indole nitrogen is optionally protected by an amino protecting group;
 b) covalently attaching noribogaine to a solid support via the hydroxyl group of noribogaine so as to form a suspension of solid supports having noribogaine bound thereto;
 c) removing residual ibogaine from said suspension;
 d) cleaving and recovering noribogaine from the solid support; and
 e) optionally repeating steps b), c) and d) up to 5 times;
 f) purifying noribogaine as recovered per above.

In another of its method aspects, this invention is directed to a method for preparing and purifying noribogaine which method comprises:
 a) covalently attaching ibogaine to a solid support via the amino group of ibogaine so as to form a suspension of solid supports having ibogaine bound thereto;
 b) converting ibogaine to noribogaine under conditions wherein the level of ibogaine bound to the solid support is less than 0.1 weight percent;
 c) cleaving and recovering noribogaine from the solid support; and
 d) purifying noribogaine as recovered per above.

In one of its composition aspects, this invention is directed to a solid support having ibogaine or noribogaine covalently bound thereto through a cleavable linker In one embodiment, the solid support of this invention comprises ibogaine covalently bound thereto through a cleavable linker. In another embodiment, the solid support of this invention comprises noribogaine covalently bound thereto through a cleavable linker.

DETAILED DESCRIPTION OF THE INVENTION

This invention is directed to methods and compositions comprising noribogaine and, in particular, methods and compositions comprising highly pure noribogaine. However, prior to describing this invention in greater detail, the following terms will first be defined.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims."

It must be noted that as used herein and in the appended claims, the singular forms "a", "an", and "the" include plural referents unless the context clearly dictates otherwise. Thus, for example, reference to "a pharmaceutically acceptable excipient" includes a plurality of such excipients.

1. Definitions

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

As stated above, the invention is directed to compositions comprising noribogaine and an excipient to facilitate transport across the blood brain barrier.

As used herein, the term "noribogaine" refers to the compound:

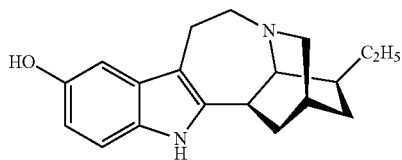

and salts thereof. Conventionally, noribogaine is prepared by demethylation of naturally occurring ibogaine:

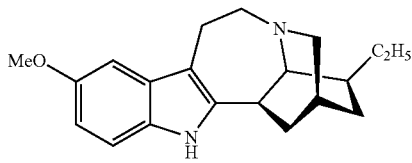

which is isolated from *Tabernanth iboga*, a shrub of West Africa. Demethylation may be accomplished by conventional techniques such as by reaction with boron tribromide/methylene chloride at room temperature, or reaction with lithium diphenylphosphine (preferably an excess thereof), followed by conventional purification. This invention is not limited to any particular chemical form of noribogaine and the compound may be present as either as a free base or as an acceptable addition salt.

The term "solid support" refers to a material having a rigid or semi-rigid surface which contain or can be derivatized to contain reactive functionality which covalently links noribogaine or ibogaine to the surface thereof through a cleavable linker. Such materials are well known in the art and include, by way of example, silica, synthetic silicates, biogenic silicates, porous glass, hydrogels, silicate-containing minerals, synthetic polymers, polystyrene, polypropylene, polyacrylamide, polyethylene glycol, polyacrylamide and copolymers thereof including copolymers of polystyrene/polyethylene glycol and polyacrylamide/polyethylene glycol, and the like.

As used herein, the term "ion exchange resin" refers to an insoluble organic polymer containing charged groups that attract and hold oppositely charged ions present in a surrounding solution in exchange for counterions previously held. Suitable ion exchange resins to be used herein contain cationic groups that attract and hold anions present in a surrounding solution, and are sometimes referred to as "anion exchange resins".

As used herein, the term "cleavable linking arms" refers to linking arms, which are a chemical group or a covalent bond which covalently attaches at one end to a solid support and at the other end to ibogaine or noribogaine. At least one of the covalent bonds of the linking arm which attaches ibogaine or noribogaine to the solid support can be readily broken by specific chemical or enzymatic reactions, thereby providing for ibogaine or noribogaine free of the solid support. The chemical or enzymatic reactions employed to break the covalent bond of the linking arm are selected so as to be specific for bond breakage thereby preventing unintended reactions occurring elsewhere on the compound. The cleavable linking group is selected relative to ibogaine/noribogaine formed on the solid support so as to prevent premature cleavage of either ibogaine or noribogaine from the solid support as well as not to interfere with any of the procedures employed during synthesis on the support. Suitable cleavable linking arms are well known in the art, and may include such groups as carbonate groups, carbamate groups, amide groups, and the like. In a preferred embodiment, the cleavable linker arm contains no more than 10 atoms. More preferably, the cleavable linker contains from 1 to 4 carbon atoms and from 2 to 4 heteroatoms selected from oxygen, nitrogen, sulfur, $S(O)$ and $S(O)_2$.

As used herein, the term "an acceptable addition salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

As used herein, the term "protecting group" or "Pg" refers to well known functional groups which, when bound to a functional group, render the resulting protected functional group inert to the reaction conditions to be conducted on other portions of the compound and which, at the appropriate time, can be reacted to regenerate the original functionality. The identity of the protecting group is not critical and is selected to be compatible with the remainder of the molecule. In one embodiment, the protecting group is an "amino protecting group" which protects the amino functionality of ibogaine or noribogaine during the reactions described herein. Examples of conventional amino protecting groups include, for instance, benzyl, acetyl, oxyacetyl, carboxybenzyl (Cbz), and the like. In another embodiment, the protecting group is a "hydroxy protecting group" which protects the hydroxyl functionality of noribogaine. Examples of hydroxyl protecting groups include, for instance, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, Protective Groups in Organic Synthesis., 2d Ed., 1991, John Wiley & Sons, and McOmie Protective Groups in Organic Chemistry, 1975, Plenum Press.

Preparation and Purification of Noribogaine

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Fourth Edition, Wiley, N.Y., 2007, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

It is contemplated that noribogaine can be prepared and/or purified from ibogaine by utilizing solid support as shown in the following Schemes, where PG represents an amine protecting group, LG represents a leaving group (e.g. a halo or alcohol), L represents a cleavable linking group (e.g. a carbonyl compound such as a carbonate or carbamate) and the shaded circle represents a solid support. In the following Schemes, the O-demethylation of the aryl methoxy group to provide the corresponding phenol can be accomplishing using any suitable method known in the art. Suitable reagents include a Lewis acid (e.g. $BBr_3$, $AlCl_3$), a nucleophile (e.g. RS—, $N_3$—, SCN—), NaCN at low pH (e.g. pH 12), lithium diphenylphosphine (preferably an excess thereof), and the like. In some embodiments, the O-demethylation should be performed without affecting the linkage to the solid support. Suitable reagents can be readily ascertained by one of skill in the art and can be found, for example, in T. W. Greene and G. M. Wuts, Protecting Groups in Organic Synthesis, Fourth Edition, Wiley, N.Y., 2007 (see, e.g., the reactivity charts at pages 1006-1008 and 1022-1032), and references cited therein.

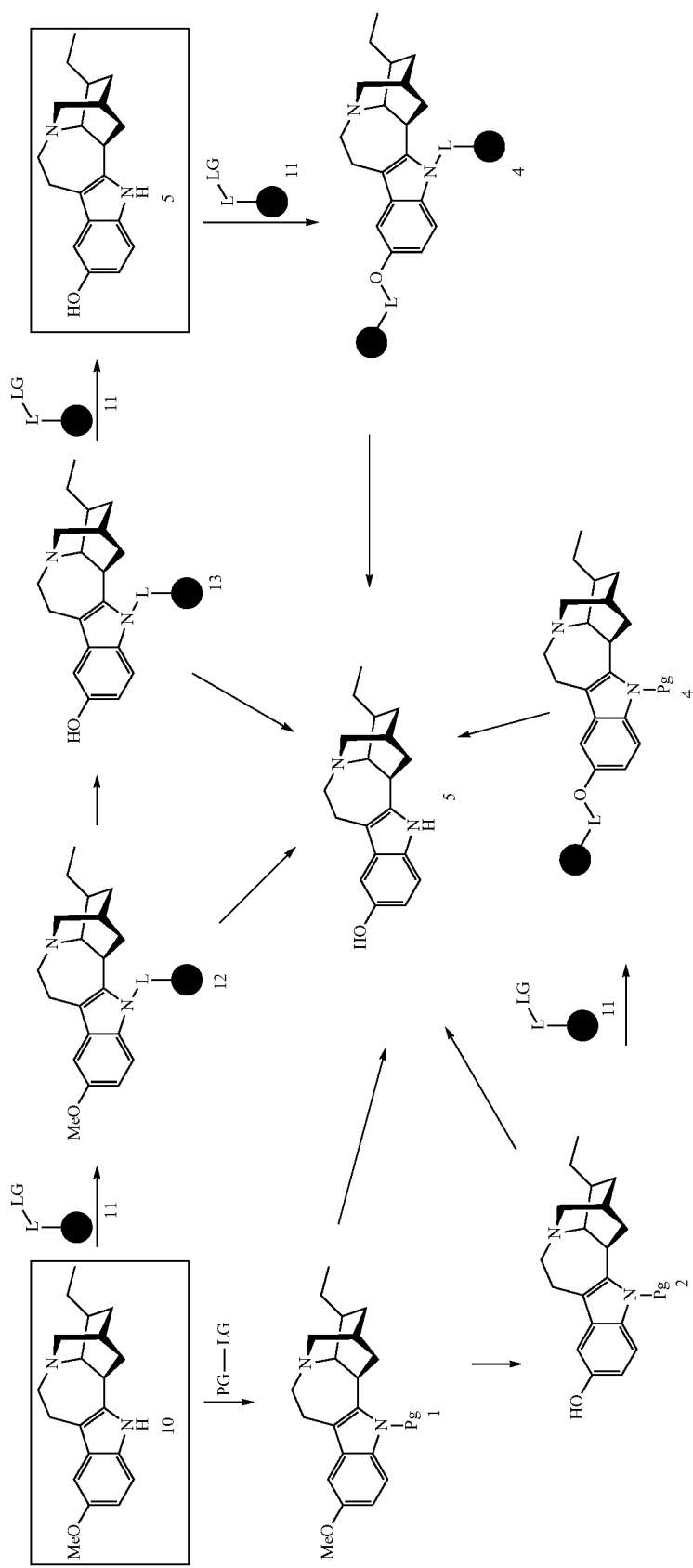
SCHEME 1

Noribogaine 5 can be prepared and purified from ibogaine 10 by any one of the routes shown in Scheme 1. Noribogaine, compound 5, is differentiated from ibogaine by virtue of the fact that the methoxy group of ibogaine has been converted to a hydroxyl group in noribogaine. In one embodiment, the indole amine of ibogaine can be protected using an amine protecting group to provide compound 1, followed by either tandem O-demethylation and removal of the protecting group using L-selectride®, for example, or sequential O-demethylation and removal of the protecting group to provide noribogaine 5. In addition, in one embodiment, noribogaine can be directly prepared and purified from the O-demethylation of ibogaine using methods known in the art and then purified by appending noribogaine to a solid support (compound 12 or 13), washing any contaminants, cleaving the linking group L, and recovering the noribogaine 5. In the above syntheses, one or more of the noribogaine or intermediates shown above can be purified using standard purification techniques known in the art (e.g. column chromatography, HPLC, and the like). Compounds of formula II are commercially available or can be synthesized in one or two steps from commercially available starting materials (see, e.g. commercially available resins from Sigma-Aldrich®).

In one preferred embodiment, purification techniques can be used to maximize the purity of the recovered noribogaine. In one embodiment, noribogaine can be contacted with a suitable ion exchange resin at a pH where the phenol group has deprotonated to a sufficient degree such that these compounds are suitable for purification. Typically for phenol deprotonation, a pH of 10 or greater is used. As ibogaine does not have an ionizable phenolic group, it will not bind to the ion exchange resin and can thus be eluted from column and separated from the resin-bound noribogaine. Suitable ion exchange resins are commercially available and include Amberlite®, Toyopearl®, Lewatit®, Dowex®, Diaion™, and Amberlyst®(Sigma Aldrich, Inc.)

Accordingly, in one of its composition aspects, there is provided an aqueous solution having a pH of at least 10 and a compound of the formula:

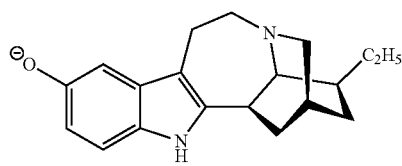

The purification process typically comprises pretreating or washing the resin with a solvent system which has the same pH, and other components such buffers, stabilizers, etc., that will be used to dissolve the noribogaine or salt thereof ("wash solvent"). Washing preferably includes passing at least 1 void volume (the volume of solvent needed to fill the resin vessel) of the wash solvent through the resin under ambient conditions. Subsequently, noribogaine is added to the same solvent system used as the wash solvent at a concentration preferably less than the saturation concentration for noribogaine. Noribogaine may be present as the phenolic anion under these conditions and, accordingly, both will bind to the anion exchange resin while other compounds lacking an anionic charge (i.e. ibogaine) will pass through the resin. Elution of the purified noribogaine can be then be accomplished using a cation-containing solution.

Accordingly, in another of its composition aspects, there is provided an anion exchange resin comprising an aqueous solvent system and a pH of at least 10 and either compound 2a or compound 4a bound thereto.

In one embodiment, noribogaine can be prepared and purified from ibogaine in the manner described in Scheme 2 below:

SCHEME 2

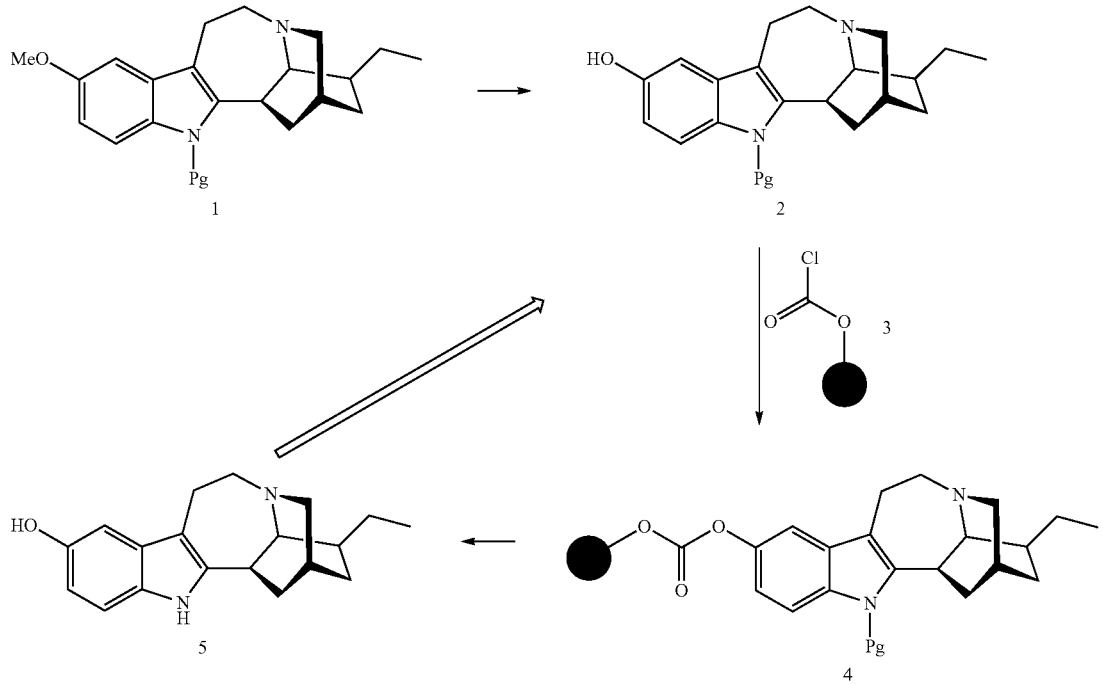

wherein Pg is hydrogen or an amino protecting group and the shaded circle represents a solid support.

Specifically, in Scheme 2, amino protected ibogaine, compound 1, is contacted with boron tribromide in methylene chloride or lithium diphenylphosphine using conditions well known in the art to provide for the amino protected noribogaine, compound 2.

In Scheme 2, attachment of amino protected noribogaine, compound 2, to a solid support is accomplished by use of a chloroformate/solid support, compound 3, under conventional conditions to provide for compound 4 wherein the carbonate group is shown for illustrative purposes only as the cleavable linking group. Other cleavable linkers can likewise be used in Scheme 2. As amino protected ibogaine does not contain a functional group reactive with compound 3, only amino protected noribogaine, compound 2, will react with the solid support and provide for compound 4. Repeated washing of compound 4 will remove amino protected ibogaine contaminating the sample of amino protected noribogaine used in this reaction. Furthermore, at any time, a small portion of the solid support can be removed to provide a sample of noribogaine (after cleavage and deprotection). The sample can then be analyzed for purity relative to any ibogaine present by conventional methods such as GC/MS, NMR, $C^{13}$-NMR, etc.

Upon achieving the desired level of purity of noribogaine relative to any contaminating ibogaine, noribogaine, compound 5, can be recovered from the solid support by cleavage of the cleavable linker and subsequent deprotection of the amino group. Both cleavage and deprotection are well known in the art.

As desired, exceptionally pure noribogaine, compound 5, can be obtained by repeating the process of forming the amino protected noribogaine, compound 2, binding compound 2 to a solid support via the hydroxyl group of amino protected noribogaine and washing any contaminating ibogaine from the solid support. By repeating this process as often as necessary and preferably no more than 5 times, it is contemplated that noribogaine having less than 5 ppm ibogaine and preferably less than 100 ppt ibogaine can be prepared.

In another embodiment, noribogaine can be prepared and purified from ibogaine in the manner described in Scheme 3 below:

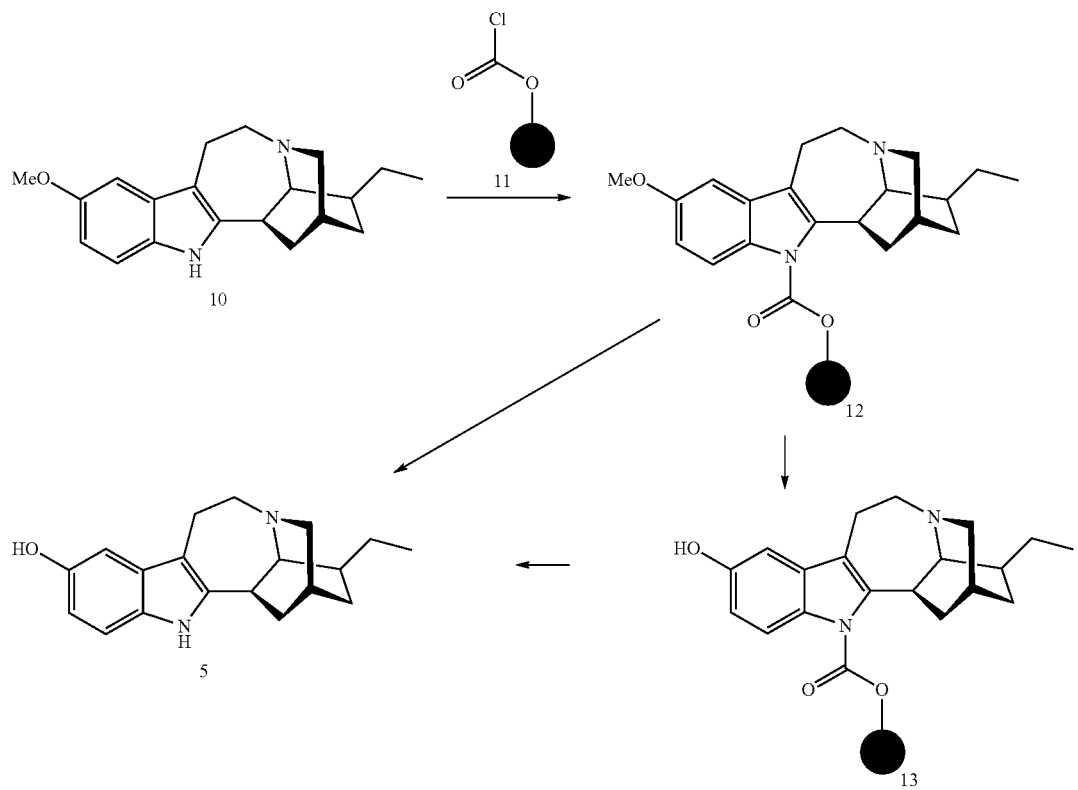

In Scheme 3, ibogaine, compound 10, is bound via conventional techniques to a solid support, compound 11, through a cleavable linker arm which, for the sake of illustration only, is depicted as a carbamate bond in resulting compound 12. Compound 12 is then contacted with boron tribromide in methylene chloride or lithium diphenylphosphine using conditions well known in the art to provide for the noribogaine bound via the indole nitrogen to a solid support, compound 13. Cleavage of the cleavable linker in compound 13 provides for noribogaine, compound 5. In certain embodiments, compound 5 can be directly obtained from compound 12 using a reducing agent (e.g. L-Selectride®). See U.S. Pat. No. 6,291,675.

In one embodiment, compound 5 can be purified by conventional techniques including high performance liquid chromatography (HPLC) and the purity level of the resulting purified compound confirmed by GC/MS. Alternatively, compound 5 can be used in Scheme 2 as recited above by attaching a solid support to the hydroxyl functionality. In either case, very high levels of noribogaine purity can be obtained.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning Example 1

Synthesis and Purification of Noribogaine from Ibogaine

Example 1 illustrates one method for the synthesis and purification of noribogaine from ibogaine which method follows Scheme 4 below:

SCHEME 4

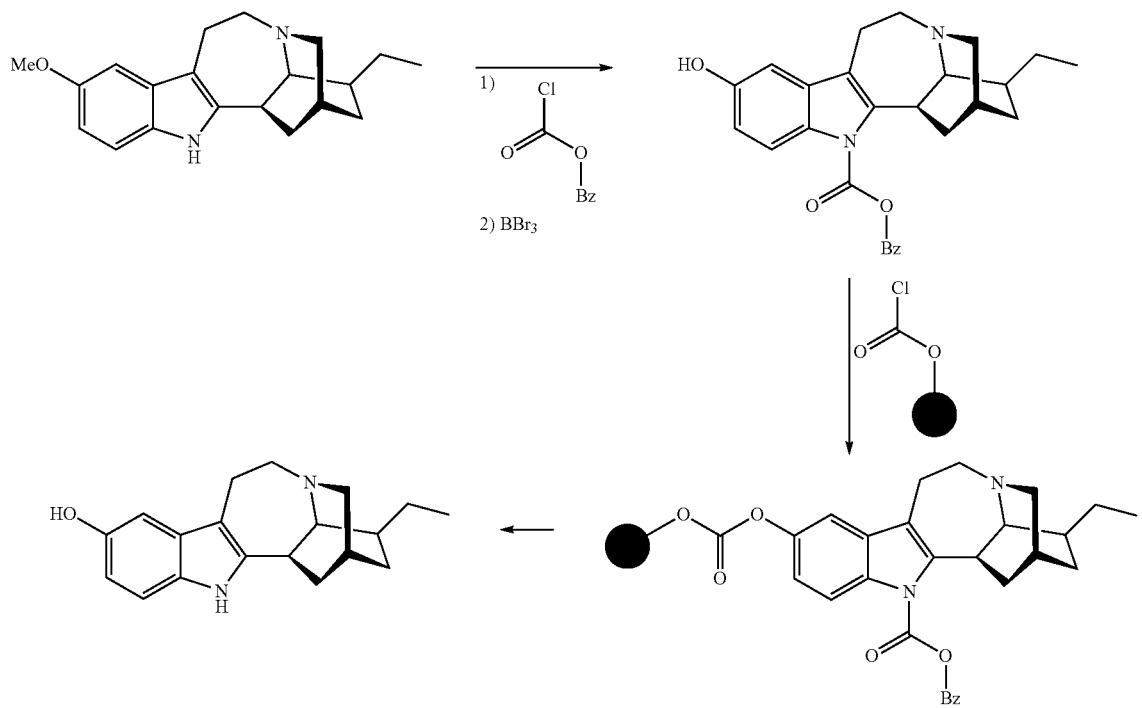

Specifically, in Scheme 4, ibogaine is contacted with a stoichiometric excess of benzyl chloroformate in an inert solvent such as methylene chloride. The reaction mixture further contains at least a stoichiometric equivalent of diisopropylethylamine relative to ibogaine so as to scavenge the acid generated during the reaction. The reaction is maintained at room temperature under an inert atmosphere until the reaction is substantially complete as evidenced by, for example, thin layer chromatograpy. At which time, an O-demethylation reagent (e.g. boron tribromide, aluminum trichloride, or lithium diphenylphosphine), or preferably a stoichiometric excess thereof, is added to the reaction mixture which is then maintained under conditions (e.g. room temperature) wherein the methoxy group of ibogaine has been converted to the hydroxyl group of noribogaine.

The hydroxyl group generated above is then employed as a complementary functionality for attachment of a solid support. In particular, an excess of chloroformate bound to a solid support is combined with N-CBZ-noribogaine under conventional conditions wherein a cleavable carbonate bond is formed. Chloroformate bound to a solid support can be prepared from a hydroxy-bearing polymer support (e.g. hydroxymethyl) polystyrene or polymer-bound benzyl alcohol, both commercially available from Sigma-Aldrich®) and carbonyl dichloride. As CBZ-ibogaine does not readily react under these O-demethylation conditions, it will remain in the solution phase of the reaction mixture and can be washed from the reaction mixture by conventional techniques including placing the solid support into a column and passing excess solvent through the column.

In one particular example, 1 kg of solid support containing CBZ-noribogaine is loaded onto a column. The stopper of the column is partially opened so that a flow rate through the column of 0.5 liters per hour is maintained. Methylene chloride is continuously fed to the top of the column and recovered at the base of the column. The recovered methylene chloride is stripped to provide residual CBZ-ibogaine. The process is continued until the effluent from the column no longer contains CBZ-ibogaine. At which time, a portion of the solid support is loaded into a hydrogenation vessel together with methanol and a catalytic amount of palladium on carbon. Hydrogenation is continued under elevated pressure for approximately 5 hours. The reaction is then stopped and the methanol recovered and stripped to provide for noribogaine. Additional purification of noribogaine can be achieved by HPLC as desired.

What is claimed is:
1. An ion exchange resin having noribogaine ionically bound thereto through an anion of noribogaine's 12-hydroxy functional group.

* * * * *